US010397529B2

United States Patent
Lu et al.

(10) Patent No.: US 10,397,529 B2
(45) Date of Patent: Aug. 27, 2019

(54) TRANSPARENT OPTICAL COUPLER ACTIVE MATRIX ARRAY

(71) Applicant: PALO ALTO RESEARCH CENTER INCORPORATED, Palo Alto, CA (US)

(72) Inventors: Jengping Lu, Fremont, CA (US); Patrick Y. Maeda, Mountain View, CA (US); Sourobh Raychaudhuri, Mountain View, CA (US); David K. Biegelsen, Portola Valley, CA (US); Eugene M. Chow, Fremont, CA (US)

(73) Assignee: Palo Alto Research Center Incorporated, Palo Alto, CA (US)

( * ) Notice: Subject to any disclaimer, the term of this patent is extended or adjusted under 35 U.S.C. 154(b) by 0 days.

(21) Appl. No.: 15/582,296

(22) Filed: Apr. 28, 2017

(65) Prior Publication Data

US 2018/0316897 A1     Nov. 1, 2018

(51) Int. Cl.
| | |
|---|---|
| *H01L 27/12* | (2006.01) |
| *H04N 5/33* | (2006.01) |
| *H04N 9/04* | (2006.01) |
| *H01L 31/112* | (2006.01) |
| *G02B 27/14* | (2006.01) |
| *G01N 21/88* | (2006.01) |
| *G02B 27/60* | (2006.01) |

(52) U.S. Cl.
CPC ............. *H04N 9/045* (2013.01); *G01N 21/88* (2013.01); *G02B 27/141* (2013.01); *H01L 27/1214* (2013.01); *H01L 31/112* (2013.01); *H04N 5/33* (2013.01); *G02B 27/60* (2013.01)

(58) Field of Classification Search
CPC .. H04N 9/045; G02B 27/1006; G02B 27/141; H01L 31/112
See application file for complete search history.

(56) References Cited

U.S. PATENT DOCUMENTS

| | | |
|---|---|---|
| 4,779,126 A | 10/1988 | Herman |
| 5,028,788 A | 7/1991 | Beland et al. |
| 5,083,175 A | 1/1992 | Hack et al. |

(Continued)

FOREIGN PATENT DOCUMENTS

| | | |
|---|---|---|
| EP | 0361515 B1 | 6/1995 |
| EP | 1711968 B1 | 7/2008 |
| KR | 20090065182 A | 6/2009 |

*Primary Examiner* — Elias Ullah
(74) *Attorney, Agent, or Firm* — Miller Nash Graham & Dunn LLP

(57) ABSTRACT

A backplane has an array of output terminals arranged on an output surface of the backplane, and an array of solid state optical switches, each optical switch corresponding to one of the output terminals, wherein the solid state optical switches are responsive to light of a control wavelength and are transparent to light of a sensing wavelength, wherein the backplane is of a material transparent to light of a sensing wavelength different from the control wavelength. An optical system includes a backplane having an array of optocouplers, a projector to generate light of a control wavelength to which the optocouplers are responsive, optics to direct the control light onto the array of optocouplers on a backplane,
an imaging system responsive to light of a sensing wavelength, wherein the backplane is at least partially transparent to the sensing wavelength.

19 Claims, 5 Drawing Sheets

(56) References Cited

U.S. PATENT DOCUMENTS

| | | | |
|---|---|---|---|
| 5,200,634 A | 4/1993 | Tsukada et al. | |
| 5,264,720 A | 11/1993 | Muto et al. | |
| 5,880,494 A | 3/1999 | Watanabe | |
| 6,885,789 B2 | 4/2005 | Liu | |
| 7,038,242 B2 | 5/2006 | Vande Voorde et al. | |
| 2008/0150069 A1 | 6/2008 | Popovic et al. | |
| 2014/0212085 A1 | 7/2014 | Margaritas | |
| 2016/0212510 A1* | 7/2016 | Bogoni | H04J 14/04 |
| 2016/0351584 A1 | 12/2016 | Lu et al. | |
| 2016/0351735 A1 | 12/2016 | Lu et al. | |
| 2017/0078513 A1 | 3/2017 | Chang et al. | |

* cited by examiner

TRANSPARENT OPTICAL COUPLER ACTIVE MATRIX ARRAY

STATEMENT REGARDING FEDERALLY SPONSORED RESEARCH AND DEVELOPMENT

This invention was made with Government support under FA8650-15-C-755 DARPA-A2P Assembler, and ARPA-E DE-AR0000631 awarded by DARPA. The Government has certain rights in this invention.

FIELD OF THE INVENTION

This disclosure relates to optocoupler arrays, more particularly to optocoupler arrays using active switching matrices.

BACKGROUND

Active matrix arrays, typically consisting of arrays of transistors, provide access to a large number of electronic elements. These arrays typically address high density light emitting elements such as a liquid crystal display (LCD) or an organic light emitting diode (OLED) display. These active matrix arrays used to access the lighting elements have been made thin to facilitate flat panel displays. Active matrix addressing can also control electronic elements actuated by high voltages. High voltage applications typically involve some type of electrical isolation between control and output circuits.

In one previous approach, set out in US Patent Publication No, 20160351584, that system addresses the backplane from one side and the actuation and sensing for the result of actuation occurs from the other side. The backplane provides light pattern separation between front and back. However, some situations benefit from actuation and sensing from the addressing side as well.

SUMMARY

One embodiment consists of a backplane having an array of output terminals arranged on an output surface of the backplane, and an array of solid state optical switches, each optical switch corresponding to one of the output terminals, wherein the solid state optical switches are responsive to light of a control wavelength, wherein the backplane is of a material transparent to light of a sensing wavelength different from the control wavelength.

Another embodiment consists of an optical system includes a backplane having an array of optocouplers, a projector to generate light of a control wavelength to which the optocouplers are responsive, optics to direct the control light onto the array of optocouplers on a backplane, an imaging system responsive to light of a sensing wavelength, wherein the backplane is at least partially transparent to the sensing wavelength.

DETAILED DESCRIPTION OF THE EMBODIMENTS

US Patent Publication No. 20160351584 ('584) discloses an active matrix back plane having thin film optocouplers. The optocouplers, or photo transistors, allow for high voltage inputs to be electrically isolated from lower voltage control systems. High voltage outputs enable many different applications such as microelectromechanical system (MEMS) devices and driving certain types of displays like liquid crystal displays.

As used here, the term optocoupler or photo transistor refers to an optical switch having a region of photosensitive material that, when exposed to light, generates a voltage that causes the switch to activate. When a pixelated light source, such as a display, activates the individual lights of the source, it actuates the corresponding switches on the backplane to cause the switches to output the high voltage input. This provides the ability to form patterns on the side of the backplane opposite the pixelated light source.

Figure 1:
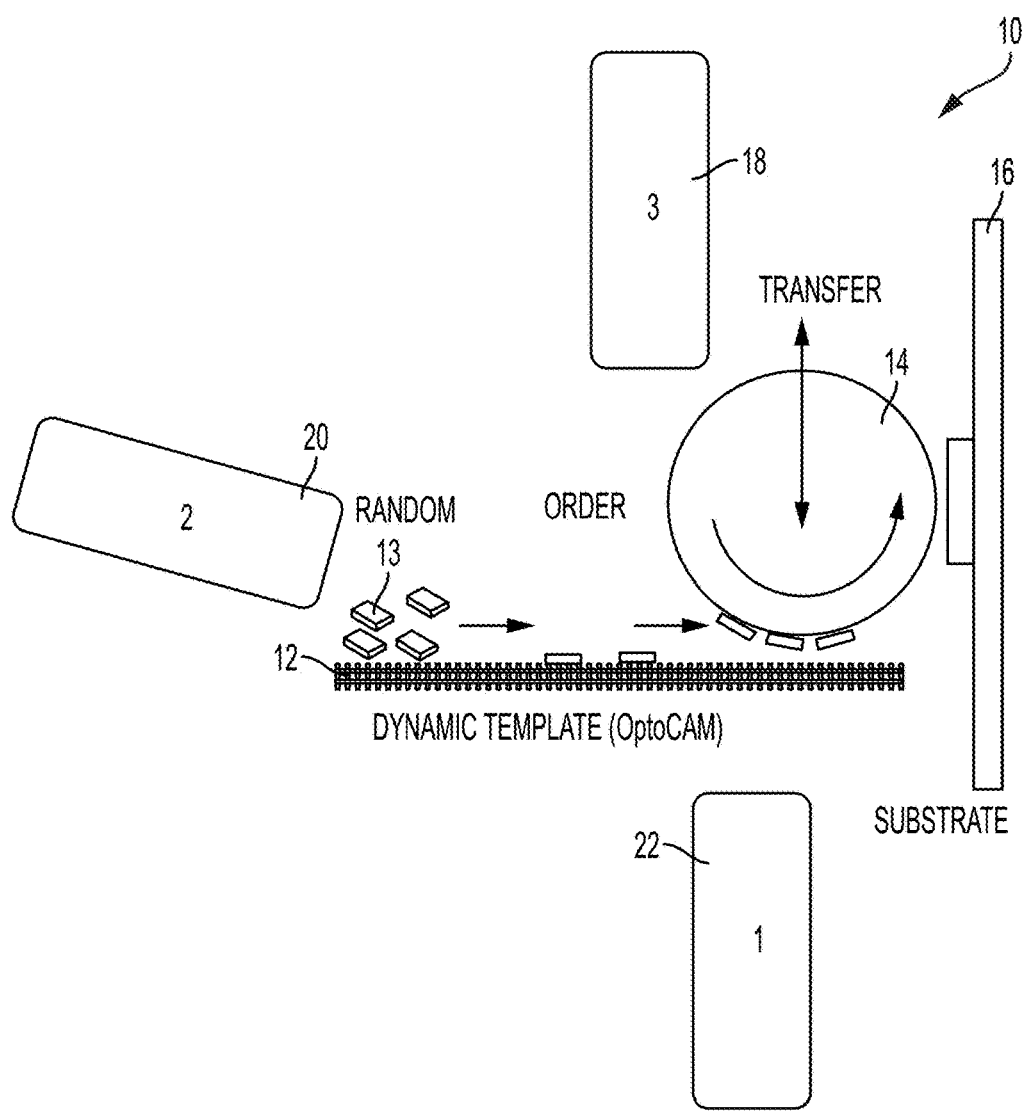
FIG. 1 shows an embodiment of an optocoupler in a chiplet sorting system.

FIG. 1 shows an example of one such application. The optocoupler active matrix 12, or OptoCAM, has a light source and generates patterns on its surface that take randomly ordered chiplets such as 13 and order them prior to their being deposited on the substrate 16. One technique used to provide feedback use vision systems such as video cameras. The camera can take one of several positions shown as 18, 20 and 22.

Position 18 cannot view the chiplets directly underneath the transfer mechanism 14, which is typically not transparent. Position 20 allows better coverage of the chiplets, but suffers from shallow oblique angles, resulting in poor image quality. Position 22 provides the best position for the most accurate images, except that the OptoCAM backplane blocks the view.

The publication '584 discusses that the OptoCAM backplane may be transparent. However, to do so becomes logically impossible. Light used to provide illumination to the imaging system would actuate the optical switches in the backplane and change the pattern, for example, in the application shown in FIG. 1. This problem will occur in any system that uses light for whatever purposes, such as the imaging system of FIG. 1.

The embodiments here separate the control light used to actuate the switches from the imaging or sensing light, which will be referred to here as the sensing light with the understand that it may be both imaging and sensing, or just one or the other. The approach here achieves this separation by wavelength. The materials in the switches consist of materials transparent at the sensing light wavelength. The wavelength and intensity of the sensing light should not induce a specified minimum photo current in the photo transistor. Most often the semiconductor has a band gap, such as for crystalline semiconductors, or low density of states energy range that is also considered a band gap, such as amorphous semiconductors. Incident light with energy above the band gap is strongly absorbed; light with energy below the band gap is weakly absorbed, generating an insignificant density of free carriers. Therefore a control illumination should generally have an energy above the band gap energy and a sensing illumination should generally have an energy below the band gap energy.

Figure 2:
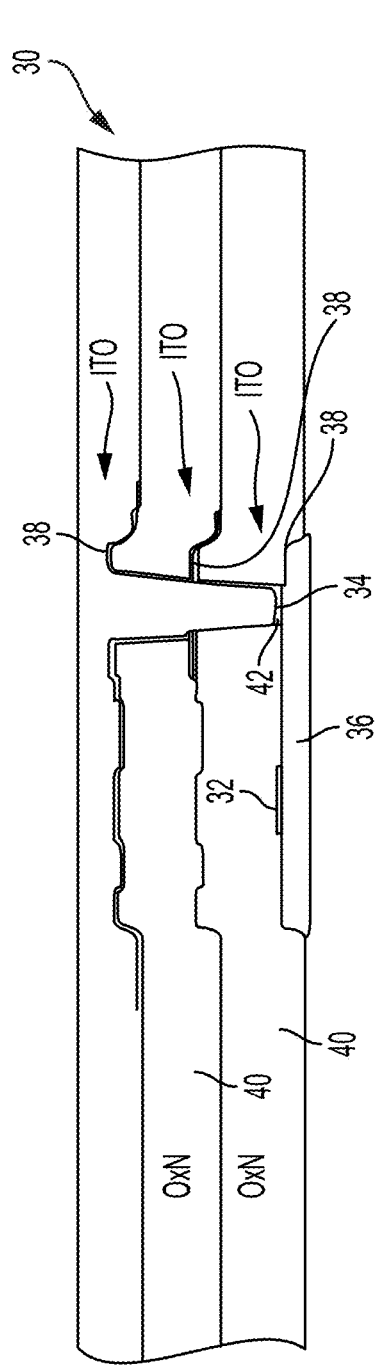
FIG. 2 shows an embodiment of a photosensitive element in a backplane.
Figure 3:
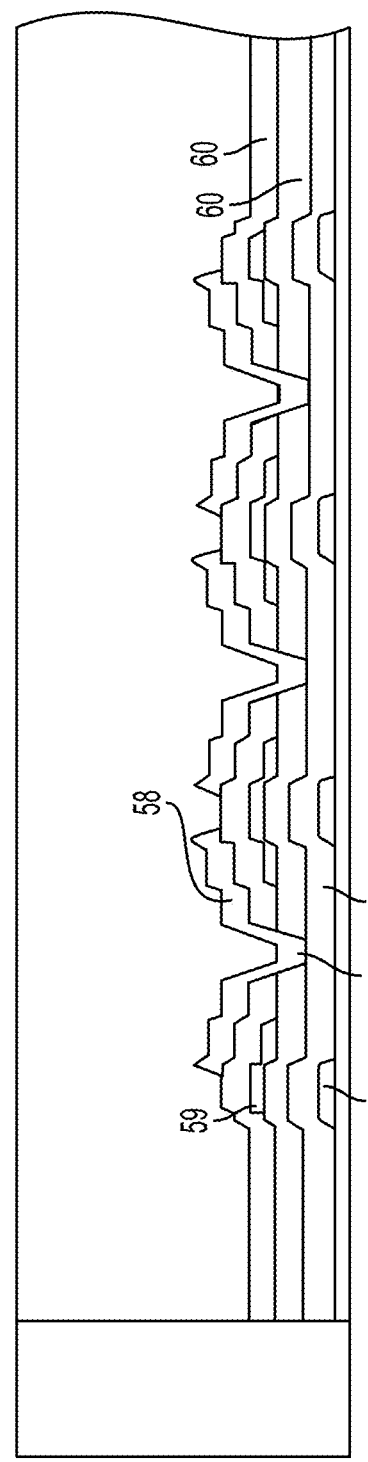
FIG. 3 shows an alternative embodiment of a photosensitive element in a backplane.

FIGS. 2 and 3 show embodiments of optical switches. In either case, the electrode, ground plane, and high voltage consist of indium tin oxide (ITO) instead of typical metals. FIG. 2 shows an element 30, having a source 32 and a drain 34. A photosensitive material 36 reacts to the light at the control light, but not at the sensing light wavelength. In this embodiment, the materials for the source, drain and the layers 38 consist of ITO, and the layers 40 and the small region 42 between the photosensitive material 36 and the drain 34 consist of an oxide or nitride dielectric. In one embodiment, the photosensitive material consists of amorphous silicon.

In FIG. 3, the photo transistor only has 6 layers. The photosensitive component 56 consists of a 2000 angstrom thick layer, possibly of amorphous silicon. The layers 58 and 59 consist of indium tin oxide. In one embodiment, layers 58 may have a thickness 1000 angstroms, and layer 59 may have a thickness of 500 angstroms. The source 52 may have a thickness of 500 angstroms of ITO, and the drain 54 is at the bottom of layer 58.

Figure 4:
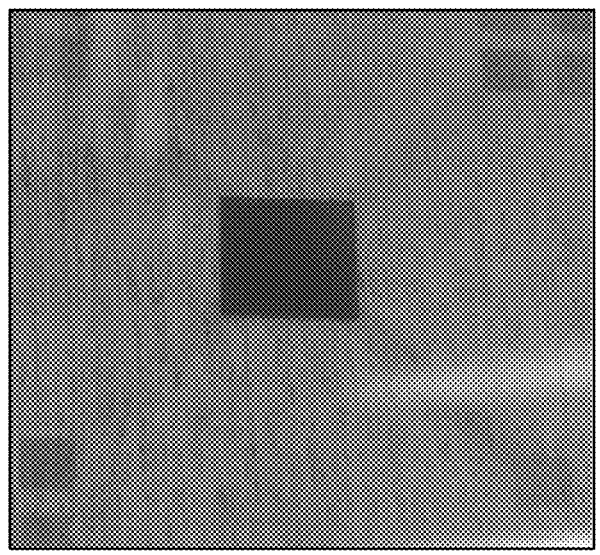
FIGS. 4 and 5 show photographs of pictures taken through an OptoCAM device.
Figure 5:
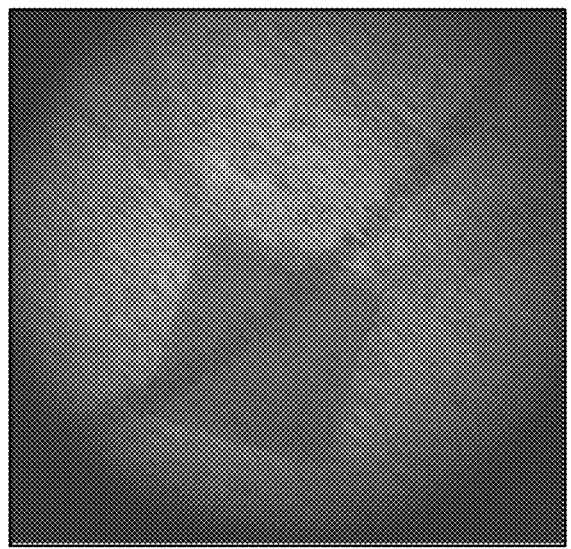

For the embodiments of FIGS. 2 and 3, in the examples of ITO, the sensing light has a wavelength in the near infrared (NIR) range, approximately 780 nanometers. At this wavelength the OptoCAM becomes effectively transparent. FIGS. 4 and 5 show different images taken of the OptoCAM device. FIG. 4 shows a visible light photo, showing the photosensitive region in the center. FIG. 5 shows a line drawn on a piece of paper photographed through the OptoCAM device at NIR wavelengths.

Figure 6:
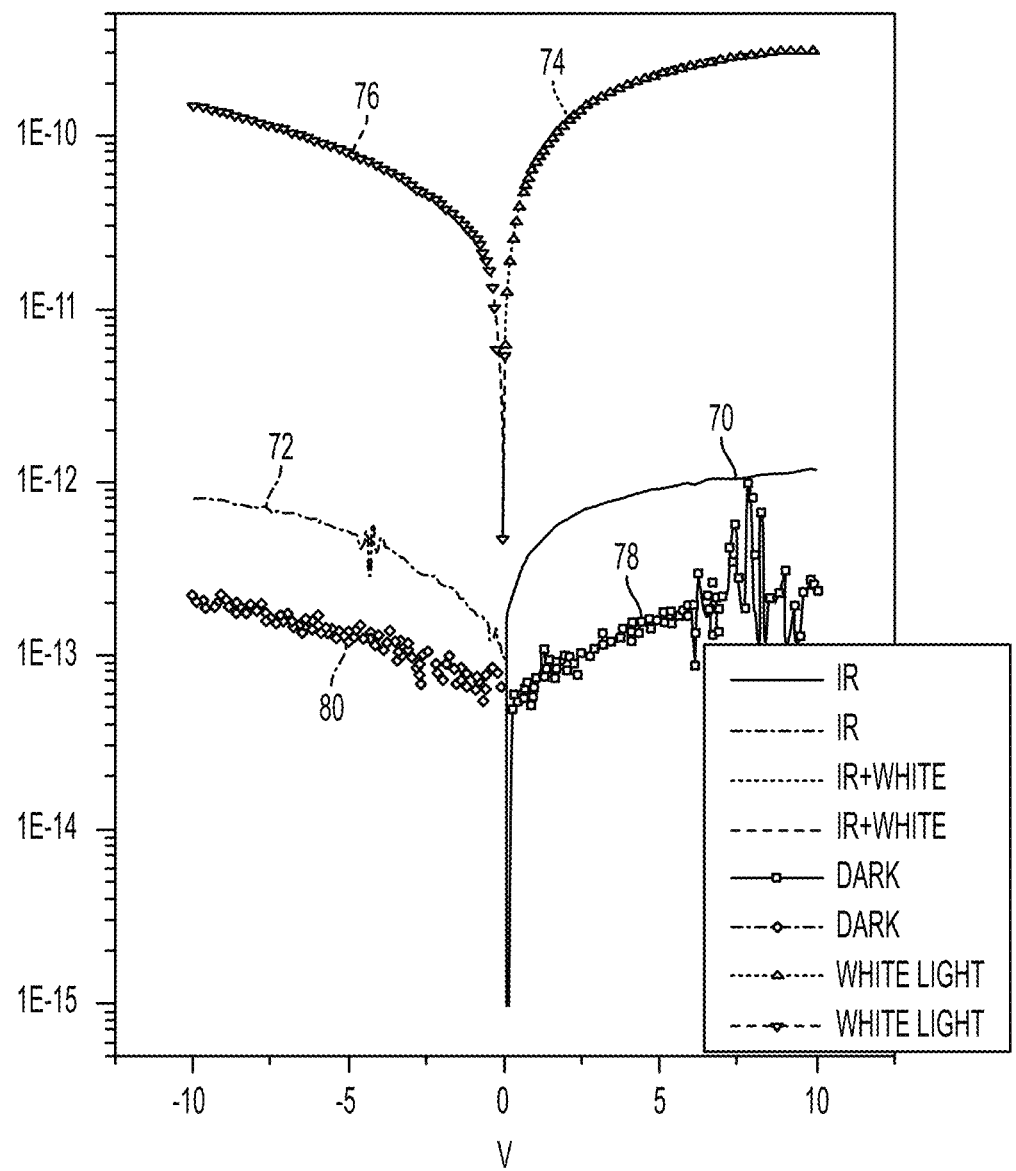
FIG. 6 shows a graph of current-voltage curves for one phototransistor.

FIG. 6 shows the current-voltage (IV) curves comparison of one photo transistor under dark and flooded with IR light, where IR light includes NIR. An on/off ratio that is greater than 100 is achieved even when the device is flooded by IR light. The curves are infrared 70, infrared 72, IR plus white that overlays a white light curve 74, curve 76 shows white light and IR plus white light, curve 78 dark and 80 shows dark. The control light used to generate these curves was visible white light provided by a typical LCD panel and the sensing light is IR. In this embodiment, "ON" means that the control light is on and "OFF" means that it is either dark (no light on), or IR. The on/off ratio, which is the current ratio at the same voltage, improves to even higher values with the use of longer NIR wavelengths such as 880 nanometer light.

In one embodiment, the OptoCAM receives the sensing light continuously. In this case, the control light could be white or green, with sensing light in the NIR range. In other embodiments, the OptoCAM may be transparent to multiple wavelengths of light sensing light and/or multiple wavelengths of control light.

Figure 7:
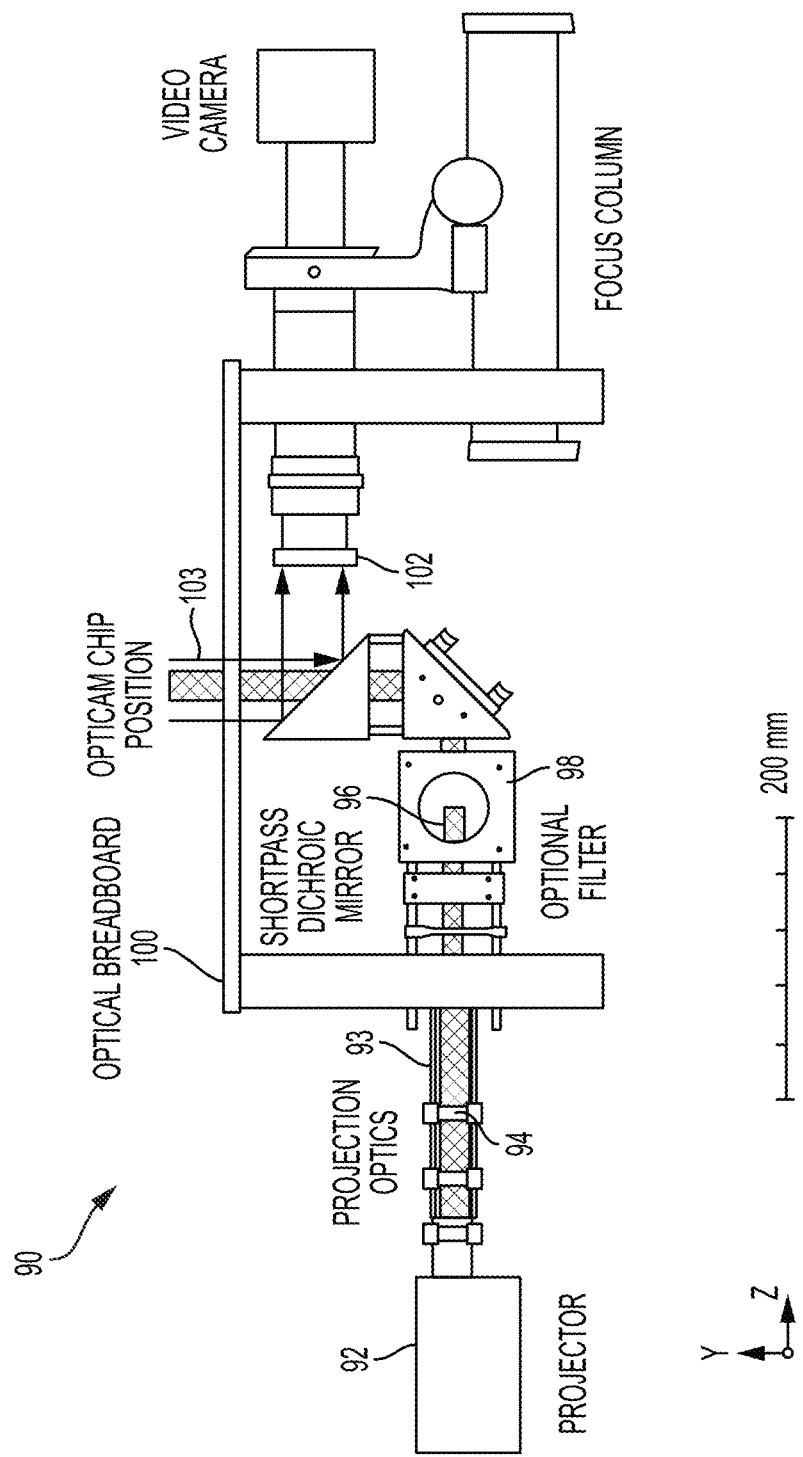
FIG. 7 shows an optical system using an optical active matrix backplane using two different wavelengths of light.

FIG. 7 shows an optical system 90. The system has a projector 92 with projection optics 94. The projector may consist of an array of light emitting elements, such as an array of LCD cells, LEDs, etc. The array of LCD cells may be a display panel. The control path includes a dichroic mirror 96 and other optical components 98. The control light 93, directed to the array of phototransistors in an aligned, image-wise matter, controls the on/off of the phototransistors of the OptoCAM 100. The sensing light 103 reflects off the chips, and then reflects off the dichroic filter into the lens of the video camera 102. The optical components may include a long pass edge filter to block any control light leakage into the video camera path. The video camera path is shown as path 104. In one embodiment, the sensing light can be added at the dichroic mirror 96, then reflected off the assembled objects and collected by the video camera.

Many different modifications may exist. For example, the embodiments assume the use of short wavelengths for control and addressing light, and longer wavelength sensing light. However, any set of orthogonal wavelengths may be used as long as the control light is absorbed by the semiconductor and the control light is not. "Orthogonal wavelengths" do not overlap, so the wavelengths for control and sensing do not overlap. For any wavelength in the control light, the amplitude for sensing is zero. For example, the control light may have wavelengths in the red or blue ranges, with sensing light having green or NIR wavelengths. Mirrors and filters with well-defined passbands are mature technology and the designer may configure the system to satisfy different requirements.

In addition, the materials used may be modified. For example, the phototransistor semiconductor could be replaced with an organic semiconductor, an inorganic oxide based semiconductor such as InGaZnO, etc., or a crystalline semiconductor like GaP (gallium phosphide). The ITO layers could be replaced with zinc oxide (ZnO), carbon nanotubes (CNT) networks, etc.

Further, the materials may be selected, different areas of the arrays may be manufactured from different materials in different regions, or the materials used may have different transparency properties, resulting in a range of transparency for the OptoCAM back plane. For example, the OptoCAM could be built with materials opaque to the sensing light occupying less than 50% of the device area, less than 30% of the backplane or device area, or less than 10% of the device area. The OptoCAM could have no material opaque to the sensing light, resulting in a device that is effectively completely transparent to the sensing light. In one embodiment, one or more backplane surfaces are coated with dielectric layers of controlled optical reflectivity at the sensing and control wavelengths.

In this manner, the flexibility of an OptoCAM backplane increases with the ability to separate control light from sensing light. One can use a vision system with many more options for positioning, as well as other illumination or imaging applications.

It will be appreciated that variants of the above-disclosed and other features and functions, or alternatives thereof, may be combined into many other different systems or applications. Various presently unforeseen or unanticipated alternatives, modifications, variations, or improvements therein may be subsequently made by those skilled in the art which are also intended to be encompassed by the following claims.

What is claimed is:

1. A backplane, comprising:
   an array of output terminals arranged on an output surface of a backplane; and
   an array of solid state optical switches, each optical switch corresponding to one of the output terminals, wherein the solid state optical switches are responsive to light of a control wavelength, wherein the control wavelength actuates the optical switches, and transparent to light of a sensing wavelength, wherein the sensing wavelength forms images, different from the control wavelength wherein the backplane is of a material having at least an area that is transparent to light of the sensing wavelength.

2. The backplane of claim 1, further comprising an input voltage connected to the array of solid state optical switches, such that when selected ones of the optical switches are actuated by light of the control wavelength the input voltage is coupled to the output terminals.

3. The backplane of claim 1, wherein the control wavelength comprises and the sensing wavelength comprise light of orthogonal wavelengths.

4. The backplane of claim 3, wherein the control wavelength comprises green light and the sensing wavelength comprises near infrared light.

5. The backplane of claim 1, wherein at least one of the backplane surfaces are coated with dielectric layers of controlled optical reflectivity at the sensing and control wavelengths.

6. The backplane of claim 1, wherein the array of solid state optical switches includes photosensitive semiconductor layers of a material selected from a group consisting of: amorphous silicon, organic semiconductors, inorganic oxide phototransistors, InGaZnO, and GaP.

7. The backplane of claim 1, wherein the backplane has material opaque to the sensing wavelength occupying less than 50% of the area of the backplane.

8. The backplane of claim 1, wherein the backplane has material opaque to the sensing wavelength occupying less than 30% of the area of the backplane.

9. The backplane of claim 1, wherein the backplane has material opaque to the sensing wavelength occupying less than 10% of the area of the backplane.

10. The backplane of claim 1, wherein the backplane has no material opaque to the sensing wavelength.

11. The backplane of claim 1, wherein the optical switches do not respond to light of the sensing wavelength.

12. An optical system, comprising:
a backplane having an array of optocouplers;
a projector to generate light of a control wavelength to which the optocouplers are responsive;
optics to direct the control light onto the array of optocouplers on a backplane in an aligned image-wise manner and cause the optocouplers to actuate; and
an imaging system responsive to light of a sensing wavelength, wherein the backplane has at least an area that is transparent to the sensing wavelength, the imaging system forms images from the light of the sensing wavelength.

13. The optical system of claim 12, further comprising at least one dichroic mirror in a path of the light from the projector to one of either combine or separate the control light and the sensing light.

14. The optical system of claim 12, wherein the imaging system comprises a vision system having a video camera.

15. The optical system of claim 13, wherein a video camera is arranged to receive light reflected from the dichroic mirror.

16. The optical system of claim 12, wherein the optocouplers do not respond to light of the sensing wavelength.

17. The optical system of claim 12, wherein the projector comprises an array of light emitting elements.

18. The optical system of claim 17, wherein the array of light emitting elements comprises an LCD display panel.

19. The optical system of claim 17, wherein the array of light emitting elements comprises an array of LEDs.

* * * * *